(12) United States Patent
Schick et al.

(10) Patent No.: US 9,568,420 B2
(45) Date of Patent: Feb. 14, 2017

(54) OPTICAL SENSORS FOR MONITORING BIOPHARMACEUTICAL SOLUTIONS IN SINGLE-USE CONTAINERS

(71) Applicant: Parker-Hannifin Corporation, Cleveland, OH (US)

(72) Inventors: Karl G. Schick, Madison, WI (US); David Uhen, Burlington, WI (US)

(73) Assignee: Parker-Hannifin Corporation, Cleveland, OH (US)

( * ) Notice: Subject to any disclaimer, the term of this patent is extended or adjusted under 35 U.S.C. 154(b) by 81 days.

(21) Appl. No.: 14/334,025

(22) Filed: Jul. 17, 2014

(65) Prior Publication Data

US 2014/0353516 A1 Dec. 4, 2014

Related U.S. Application Data

(62) Division of application No. 13/072,448, filed on Mar. 25, 2011, now Pat. No. 8,817,259.

(51) Int. Cl.
*G01N 21/00* (2006.01)
*G01N 21/51* (2006.01)
(Continued)

(52) U.S. Cl.
CPC .......... *G01N 21/51* (2013.01); *G01N 21/0303* (2013.01); *G01N 21/05* (2013.01);
(Continued)

(58) Field of Classification Search
CPC ....... G01N 21/05; G01N 21/532; G01N 21/51
See application file for complete search history.

(56) References Cited

U.S. PATENT DOCUMENTS 2,324,304 A * 7/1943 Katzman ............ G01N 21/8507
250/227.11
2,892,378 A 6/1959 Canada
(Continued)

FOREIGN PATENT DOCUMENTS

DE 4 242 927 6/1994
EP 2 012 323 A2 7/2009
(Continued)

OTHER PUBLICATIONS

Wong et al., Radiation Hard by Design Techniques for EEPROM, 12th NASA Symposium on FLSI Design, Doeurd'Alene, Idaho, Oct. 4-May 2005.
(Continued)

*Primary Examiner* — Kara E Geisel
*Assistant Examiner* — Rufus Phillips
(74) *Attorney, Agent, or Firm* — Cook Alex Ltd.

(57) ABSTRACT

Disposable, pre-sterilized, and pre-calibrated, pre-validated sensors are provided. The sensor comprises a disposable fluid conduit or bioreactor bag and a reusable sensor assembly. An optical bench or inset optical component or module is integrated within the disposable fluid conduit or bioreactor bag, which provides an optical light path through the conduit or bag. These sensors are designed to store sensor-specific information, such as calibration and production information, in a non-volatile memory chip on the disposable fluid conduit or bag and on the reusable sensor assembly. Methods for calibrating the sensor and for determining a target property of an unknown fluid are also disclosed. The devices, systems and methods relating to the sensor are suitable for and can be outfitted for turbidity sensing.

22 Claims, 7 Drawing Sheets

(51) Int. Cl.
  *G01N 21/05* (2006.01)
  *G01N 21/53* (2006.01)
  *G01N 21/85* (2006.01)
  *G01N 21/03* (2006.01)
  *G01J 1/16* (2006.01)

(52) U.S. Cl.
  CPC ....... *G01N 21/532* (2013.01); *G01N 21/8507* (2013.01); *G01J 1/1626* (2013.01); *G01N 2021/0307* (2013.01)

(56) References Cited

U.S. PATENT DOCUMENTS

| | | | |
|---|---|---|---|
| 4,040,743 | A | 8/1977 | Villaume et al. |
| 4,283,140 | A * | 8/1981 | Carson ............... G01D 3/00 356/130 |
| 4,725,148 | A | 2/1988 | Endo et al. |
| 5,140,168 | A | 8/1992 | King |
| 5,446,531 | A | 8/1995 | Boyer et al. |
| 5,485,013 | A | 1/1996 | Cummins |
| 5,596,408 | A | 1/1997 | Cummins et al. |
| 5,757,481 | A | 5/1998 | O'Brien et al. |
| 5,828,458 | A | 10/1998 | Taylor et al. |
| 5,923,433 | A | 7/1999 | Gluffre et al. |
| 6,350,382 | B1 | 2/2002 | Schick |
| 6,375,847 | B1 | 4/2002 | Hartmann |
| 6,456,375 | B1 | 9/2002 | Ottens et al. |
| 6,509,558 | B1 | 1/2003 | Loch et al. |
| 6,567,166 | B2 | 5/2003 | Ottens et al. |
| 6,712,963 | B2 | 3/2004 | Schick |
| 6,833,555 | B2 | 12/2004 | Schenkl |
| 6,842,243 | B2 | 1/2005 | Tokhtuev et al. |
| 6,891,619 | B2 | 5/2005 | Durfee et al. |
| 7,052,603 | B2 | 5/2006 | Schick |
| 7,142,299 | B2 | 11/2006 | Tokhtuev et al. |
| 7,410,587 | B2 | 8/2008 | Schick |
| 7,788,047 | B2 | 8/2010 | Schick et al. |
| 7,857,506 | B2 | 12/2010 | Schick et al. |
| 2003/0117623 | A1 | 6/2003 | Tokhtuev et al. |
| 2005/0190370 | A1 | 9/2005 | Siobanu et al. |
| 2006/0055927 | A1 | 3/2006 | Feng |
| 2006/0118472 | A1 | 6/2006 | Schick et al. |
| 2008/0241866 | A1 | 10/2008 | Korlach et al. |
| 2009/0009764 | A1 * | 1/2009 | Slepicka ............. A61M 1/28 356/370 |
| 2009/0134882 | A1 | 5/2009 | Schick et al. |

FOREIGN PATENT DOCUMENTS

| | | |
|---|---|---|
| EP | 2 392 948 A2 | 12/2011 |
| GB | 2 446934 A | 8/2008 |
| KR | 1020030068456 | 8/2003 |
| KR | 1020030066373 | 9/2003 |

OTHER PUBLICATIONS

SciCon Conductivity Sensors, Brochure, Scilog, Inc., May 4, 2009.
International Search Report and Written Opinion of International Searching Authority, Jul. 9, 2012, in PCT/US2012/029063.
Written Opinion of the International Preliminary Examining Authority, Mar. 12, 2013, in PCT/US2012/029063.
International Preliminary Report on Patentability, Aug. 13, 2013, in PCT/US2012/029063.

* cited by examiner

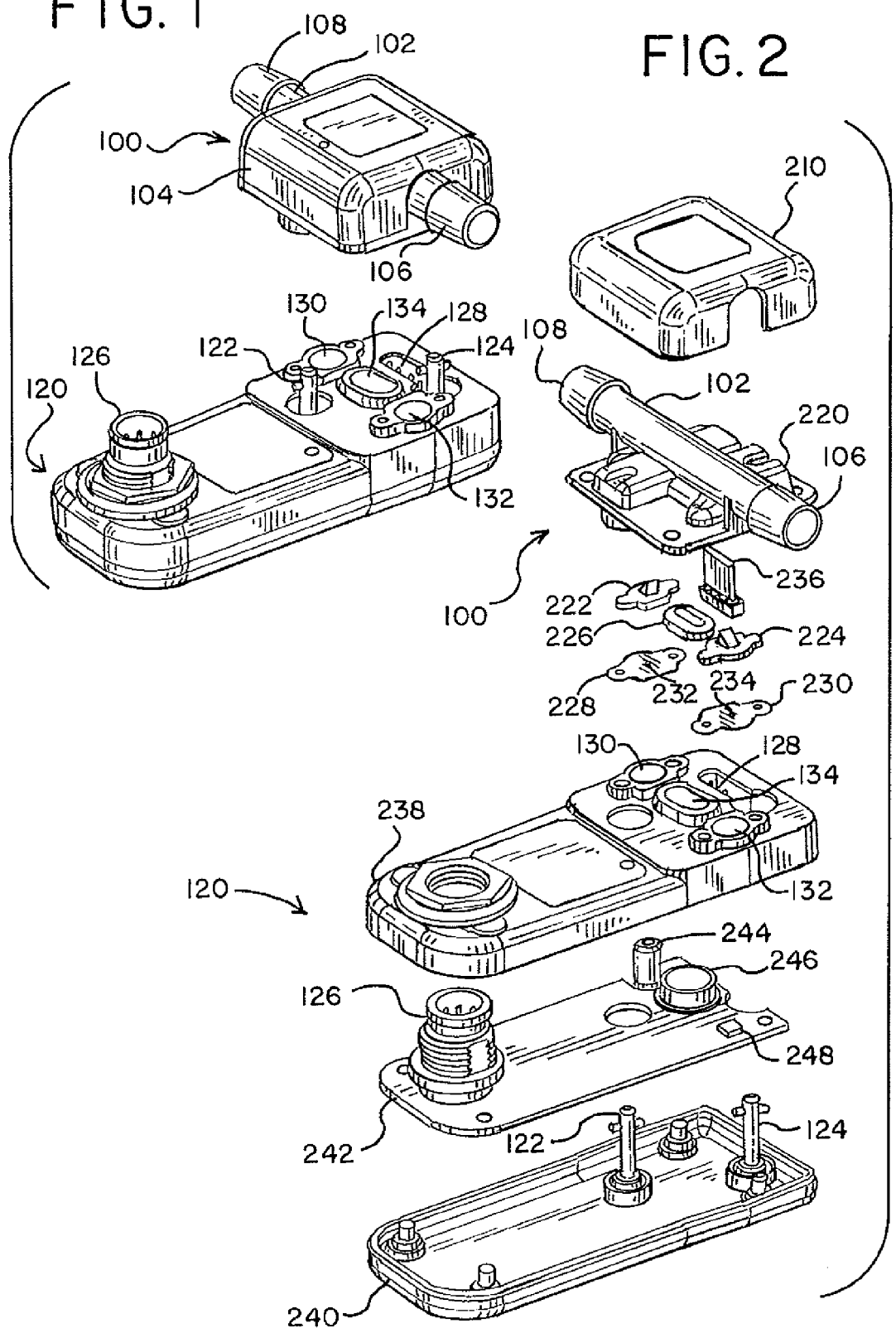

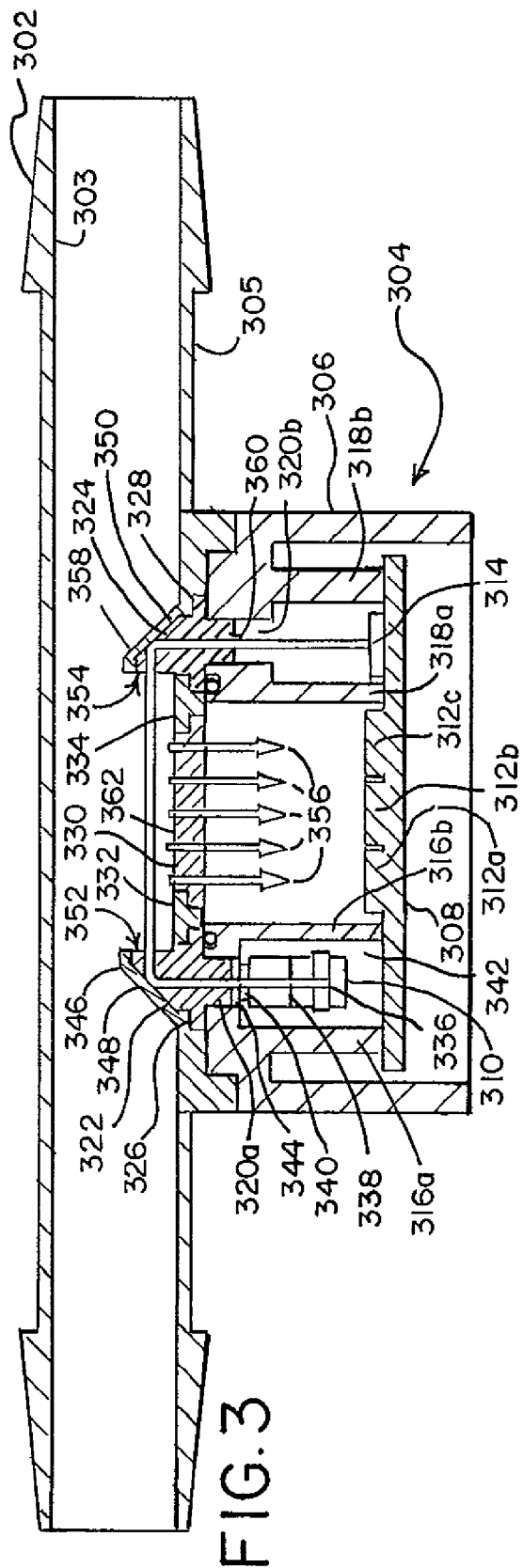
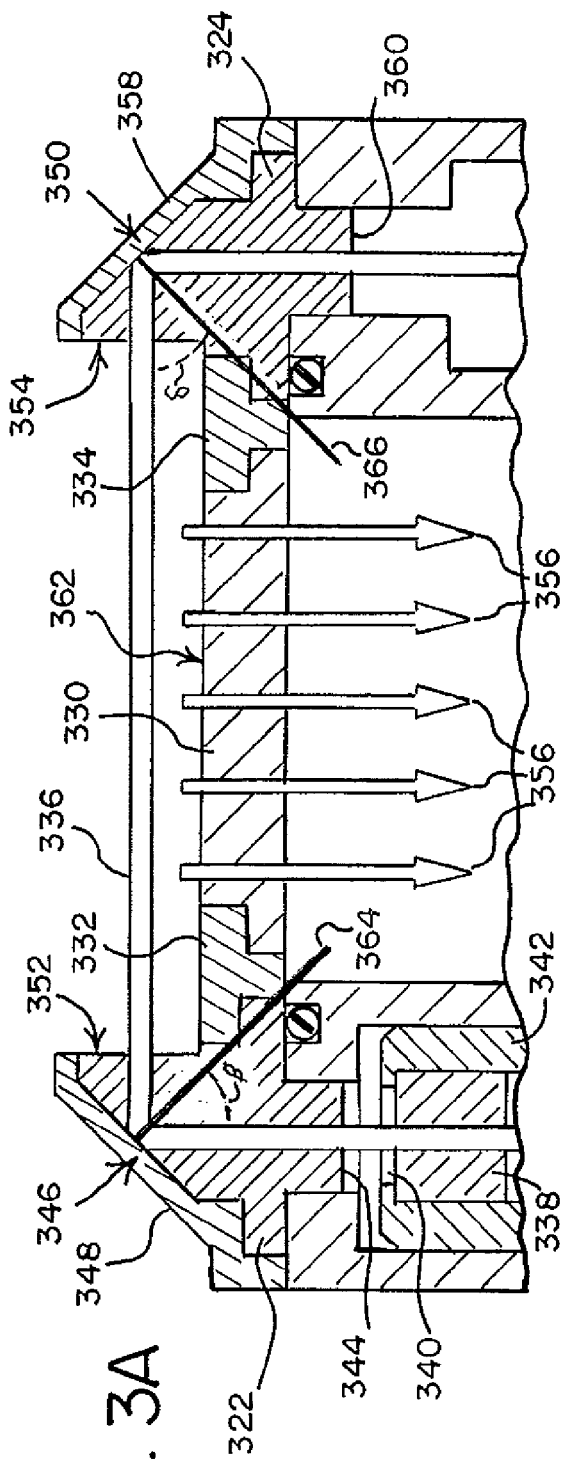

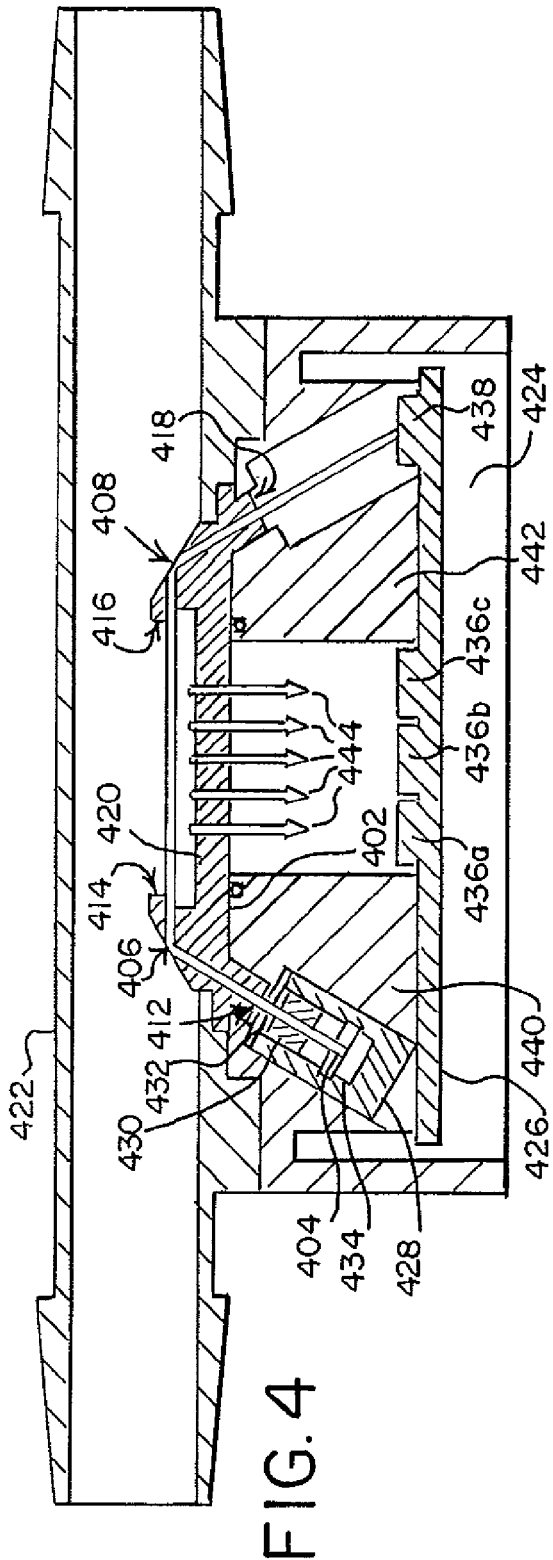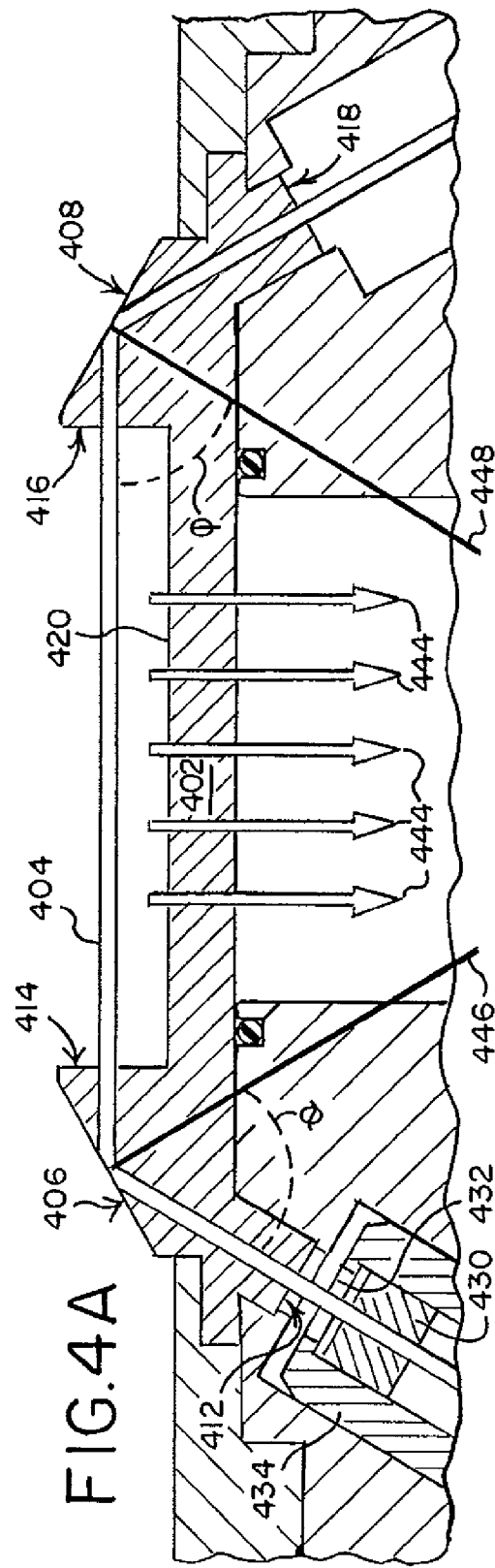

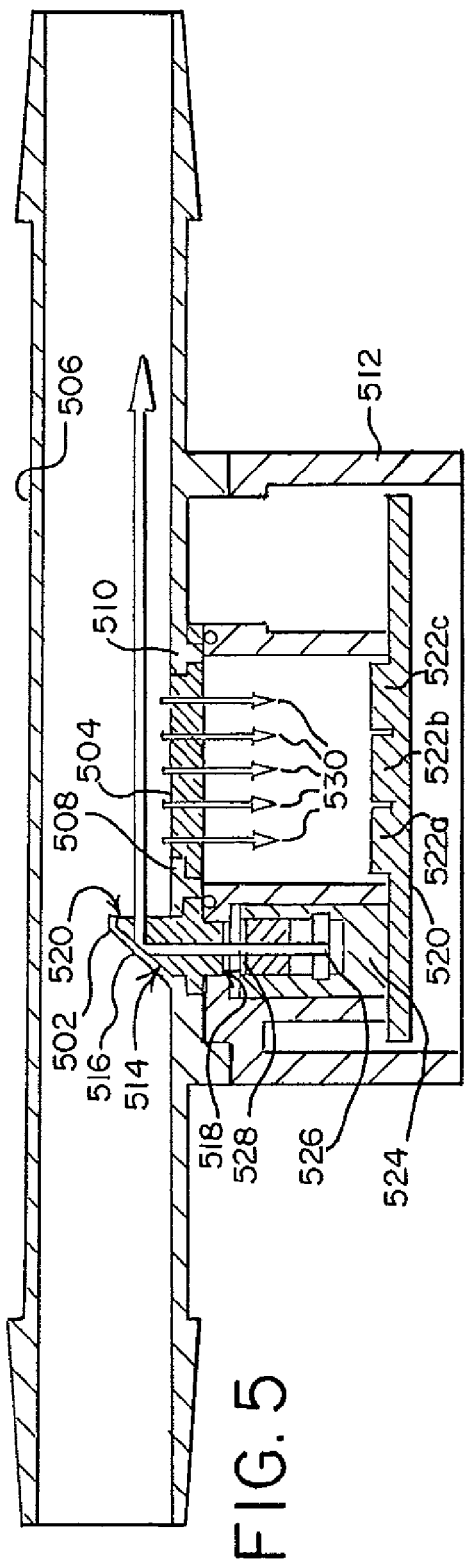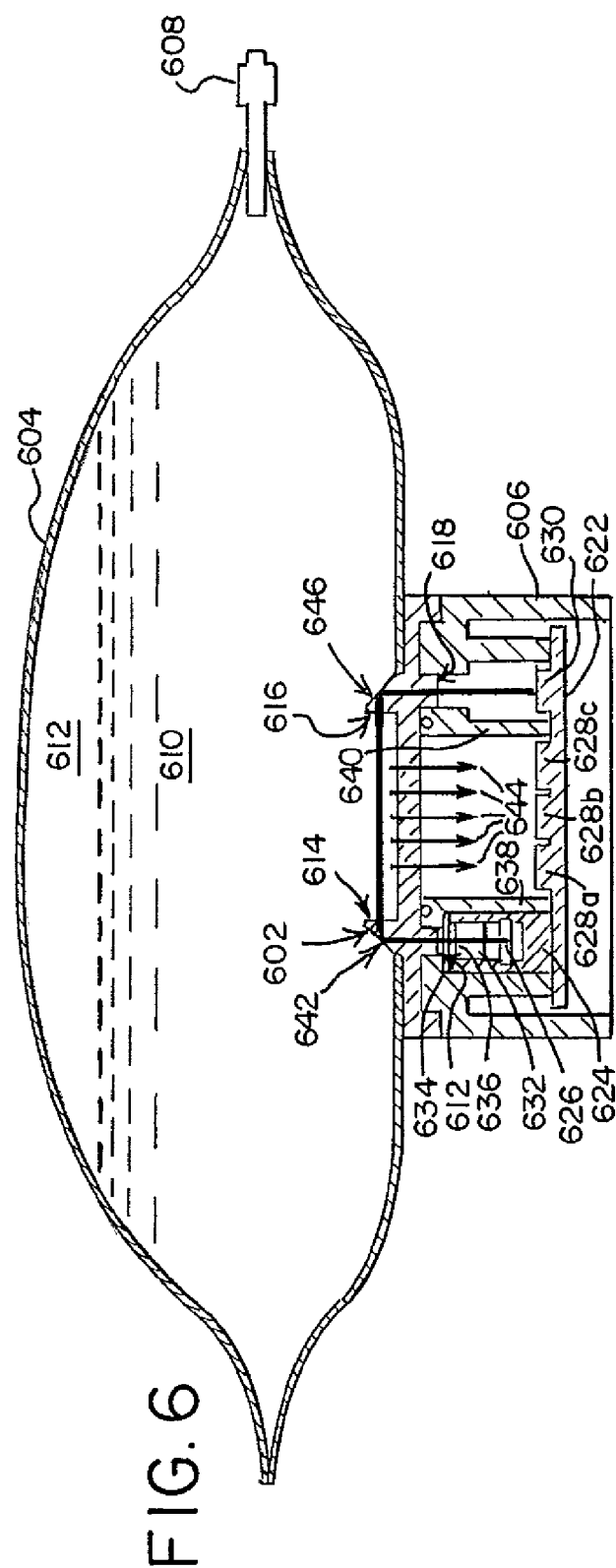

OPTICAL SENSORS FOR MONITORING BIOPHARMACEUTICAL SOLUTIONS IN SINGLE-USE CONTAINERS

FIELD OF THE INVENTION

The invention generally relates to disposable, pre-sterilized, pre-calibrated, in-line sensors. More specifically, the invention relates to disposable, pre-calibrated, pre-validated optical sensors for monitoring biopharmaceutical solutions contained in enclosed spaces such as single-use purification platforms and disposable bioreactors.

BACKGROUND OF THE INVENTION

Biopharmaceutical as well as clinical production facilities increasingly employ single-use containers including pre-sterilized, single-use, plastic tubing and collapsible plastic bags for solution storage and bioreactor applications. In addition, the downstream processing and purification of bioreactor solutions is increasingly achieved with single-use, unit-operational platforms designed for the aseptic purification of solutions by normal flow filtration (NFF), tangential flow filtration (TFF), chromatography and bioreactor applications.

Single-use platforms for downstream biopharmaceutical purification typically consist of an integrated assembly of filter elements or columns, flexible tubing, plastic connectors and solution storage bags, segments of peristaltic pump tubing as well as integrated sensors. Such assemblies are designed and pre-assembled for a specific purification process. Special, integral plastic connectors provide aseptic hook-up to external, single-use bioreactors and/or buffer solutions. In the final configuration, all elements of the purification platform are assembled, pre-sterilized by gamma-irradiation. Dedicated peristaltic pumps are used to aseptically propel the process solution and buffers through the purification tube manifold.

Pre-sterilized, single-use bag manifolds such as those used in bio-pharmaceutical production (see for example U.S. Pat. No. 6,712,963) lack the ability to monitor and validate important, analytical solution parameters during the processing of biopharmaceutical solutions. The use of such bag manifolds, for example, in preparative chromatography or tangential flow filtration (TFF) or fluid transfer generally, is severely limited by the general lack of pre-sterilized, pre-calibrated, pre-validated in-line sensors and detectors.

In-line, flow through-type sensors and detectors are well known in industry and are extensively used in analytical laboratories, pilot plants and production facilities. Prior art in-line sensors and detectors are difficult to sterilize, require in-field calibration and validation by an experienced operator before use, and are very expensive, often costing thousands of dollars. Consequently, prior art sensors and detectors are not suited for a single-use sensor application.

The need for pre-calibrated sensors arises from the fact that sensor calibration after sterilization of the sensor-manifold assembly is not possible without danger of re-contamination. On the other hand, sensor insertion into a pre-sterilized manifold just prior to use is also problematic since it would require the maintenance of a carefully controlled aseptic environment during on-site sensor calibration, sterilization and sensor insertion process. Breakdown of aseptic conditions could result in serious process contamination and give rise to unacceptable economic losses.

In-line sensors for use in bioprocessing applications must be designed to satisfy several additional requirements. For example, they must meet government regulations regarding device traceability and validation. In addition, in-line sensors must meet the application requirements for accuracy and precision. These requirements present extra challenges and pose unique problems when the in-line sensor is to be disposable and suitable for single use as desired. Furthermore, single-use sensors must meet economic requirements, i.e. sensors must be low cost, easy to replace with negligible disposal expense.

Meeting sensor sterilization requirements represents another very significant sensor design challenge. This is especially the case, when the sensor is intended for single-use bag manifold applications such as those described in the U.S. Pat. Nos. 6,712,963, 7,052,603 and 7,410,587 and U.S. Patent Application Publication No. 2006/0118472 (all of which are incorporated herein by reference).

In order to maintain a high quality of purification to a given set of specifications, pre-calibrated, single-use in-situ sensors are used for monitoring temperature, pressure, conductivity, and other solution parameters. Such in-line (in-situ) sensors must be designed to withstand the conditions of gamma-irradiation (~35 kGy) and/or steam (~123° C.) sterilization. The sensor may also endure sanitizing by ethylene oxide gas, electron-beam irradiation or a sodium hydroxide solution.

For many single-use sensor applications, e.g. for bag manifolds, the preferred sterilization method by the industry is by gamma or electron-beam irradiation. The main advantage of gamma and electron-beam irradiation lies in that the entire, pre-assembled manifold, including bags, tubing, connectors and sensors, can be first sealed in a shipping bag and then exposed to sterilizing radiation or electron-beam bombardment. The entire manifold assembly within the shipping bag remains sterile for a rated period, unless the shipping bag is comprised during shipment or storage.

For device/performance traceability, pre-calibrated sensors must contain electronically accessible sensor ID, sensor-specific calibration data and lot-specific sensor performance data. This can be accomplished with integration of a non-volatile, gamma-stable memory device into each sensor. Sensor specific calibration information and ID number are stored in the memory device after successful factory calibration of the sensor. In addition, the calibration date stamp as well as lot-specific sensor performance data is useful information stored in the non-volatile memory. In addition, the device must have sufficient memory capacity to store relevant sensor data during processing for post-production review and analysis. See U.S. Pat. No. 7,857,506 and U.S. Pat. No. 7,788,047 (which are incorporated herein by reference).

SUMMARY OF THE INVENTION

The present invention applies to the monitoring of turbidity and other solution parameters important in biopharmaceutical processing and purification of biologically derived molecules, including proteins, living cells and systems incorporating same. The invention is also relevant to the production of personal medicine, i.e. the clinical processing and purification of patient-specific molecules including expansion and purification of autologous cells and protein. Specifically, the invention addresses the process analytical challenges that arise from the need for in-situ solution monitoring in pre-sterilized, single-use bioreactors (SUB), single-use, unit-operational purification platforms and plastic tube manifolds such as those disclosed in U.S.

Pat. Nos. 6,712,963, 7,052,603 and 7,410,587 and U.S. Patent Application Publication No. 2006/0018472.

The disclosed invention provides optical sensor technology that meets all of the industry's requirements, including those identified herein. The invention provides optical methods and devices for quantitative measurements of solution turbidity and other optical density (OD) measurements such as those typically required in normal flow filtration (NFF), tangential flow filtration (TFF), chromatography and bioreactor applications.

The subject device or system comprises a reusable sensor assembly and a disposable optical bench or inset optical component. The disposable optical component can be molded and imbedded in a disposable flowcell or storage bag. The optical bench has a fluid-contacting surface side and a detector surface side. On the fluid-contacting surface side, the optical bench is designed to set within the flowcell or bag and includes one or more appropriately shaped reflectors and includes a detector window (e.g., a scattered light window). The reflectors are optically isolated (or otherwise isolated) from the detector window, which is located adjacent to one reflector or located between two or more reflectors. The optical bench securely mates to the sensor assembly on the detector surface side of the optical bench or bench module.

The sensor assembly typically includes electro-optical components mounted onto a flat sensor printed circuit board contained within a housing. Electro-optical components of the sensor assembly typically include circuitry, a high-intensity light source (such as a laser or LED), an aperture disk, a micro lens, an optical alignment bezel, a reference detector, and a photo detector. Multiples of such components can be provided, such as multiple photo detectors. The expensive electro-optical components and associated electronics are designed as a separate, detachable module sized and structured for repeated, long-term use.

The sensor assembly can be readily connected and secured to a pre-sterilized, gamma-irradiated system via the optical bench or bench module sealingly connected to a flowcell or storage bag without compromising system sterility. After the bench module and the sensor assembly are mated such as at respective docking ports, the optical sensor may be operated to measure the solution parameter of interest, such as turbidity, particle size, pH and/or protein concentration.

The sensor operates by generating a high-intensity energy beam in the visible, near-visible or IR wavelengths. In an illustrated embodiment, the energy beam is focused by a micro-lens and passes through the aperture disk. The energy beam then passes though the detector side of the optical bench. The energy beam is reflected off a reflector and passes out of the fluid-contacting side of the optical bench and through the fluid. As the energy beam encounters solution particulate within the fluid, a portion of the photons of light are scattered by the particulate. The remaining photons may pass to a reference detector. In an embodiment, these remaining photons pass back through the fluid-contacting side of optical bench, reflect off a reflector and are measured by the reference detector. A portion of the photons scattered by the particulate travel through the transparent scattered light window of the optical bench and are measured by one or more photo detectors. A comparison and calculation of the value measured by the reference detector and the values measured by the photo detectors yields information on the solution parameter of interest, such as the turbidity of the fluid.

The optical bench or bench module may have several different configurations. Same may have a single or unitary construction, comprising of opposing, facing reflectors on the fluid-contacting side separated by a transparent detection window. On the detector side of the optical bench, the optical bench may have angled or non-perpendicular beam entrance window and optical channels or optical channels which are generally perpendicular to the transparent window.

Another configuration of the optical bench comprises separate components. In such a configuration, the opposing, facing reflectors and transparent detection window of the optical bench are each separate components sealed to the flowcell, bioreactor bag, container or storage bag.

The optical bench or bench module may also comprise a single reflector and a transparent detection window. In this configuration, the optical bench does not include a return reflector. This design configuration is particularly useful for measuring low turbidity.

The disposable flowcell or storage bag may include a printed circuit board (PCB) that includes a gamma-stable memory circuit or device. The memory circuit or device is capable of storing information such as calibration data, serial number, lot number and/or lot specific performance data associate with the disposable flowcell or storage bag. The memory device may also include an "out-of-box" performance variance value, which "out-of-box" value is a statistically derived performance variance that represents the maximum measurement error for that disposable flowcell or storage bag within a defined confidence limit.

In addition, the sensor assembly may also include a printed circuit board (PCB) that includes a gamma-stable memory circuit or device. The memory circuit or device on the sensor assembly is capable of storing identification information such as calibration data, serial number, lot number and/or lot specific performance data associate with the sensor assembly. The memory device may also include an "out-of-box" performance variance value. This "out-of-box" value is a statistically derived performance variance that represents the maximum measurement error for that sensor assembly within a defined confidence limit.

It is a general aspect or object of one or more embodiments of the present invention to provide an optical sensor.

Another aspect or object of one or more embodiments of the present invention is to provide a disposable component of the sensor suitable for one-time use, which may be integrated with other disposable equipment, including bag manifolds, employed in the separation and purification of fluids that are suitable for single-use applications.

A further aspect or object of one or more embodiments of the present invention is to provide an optical bench or optical inset component arrangement for a modular system of sensing and measuring.

An aspect or object of one or more embodiments of the present invention is to reduce the cost associated with the construction of disposable optical sensors.

Another aspect or object of one or more embodiments of the present invention is to provide a disposable component and a sensor assembly each having means to store sensor-specific information, which is not affected by sterilization techniques.

These and other objects, aspects, features, improvements and advantages of the present invention will be clearly understood through a consideration of the following detailed description.

BRIEF DESCRIPTION OF THE DRAWINGS

FIG. 1 is a perspective view of an embodiment of a disposable flowcell and a reusable sensor assembly.

FIG. 2 is an exploded perspective view illustration of the disposable flowcell and a reusable sensor assembly illustrated in FIG. 1.

FIG. 3 is a longitudinal cross-section view of one embodiment of turbidity sensor with the flowcell assembly mated to a reusable sensor assembly.

FIG. 3A is an enlarged schematic view of the optical bench portion of FIG. 3.

FIG. 4 is a longitudinal cross-section view of another embodiment of turbidity sensor with the flowcell assembly mated to a reusable sensor assembly.

FIG. 4A is an enlarged schematic view of the optical bench portion of FIG. 4.

FIG. 5 is a longitudinal cross-section view of another embodiment of turbidity sensor with the flowcell assembly mated to a reusable sensor assembly.

FIG. 6 is a longitudinal cross-section view of a disposable bioreactor bag with a glued-in optical bench mated to a sensor assembly.

DETAILED DESCRIPTION OF THE EMBODIMENTS

Figure 7:
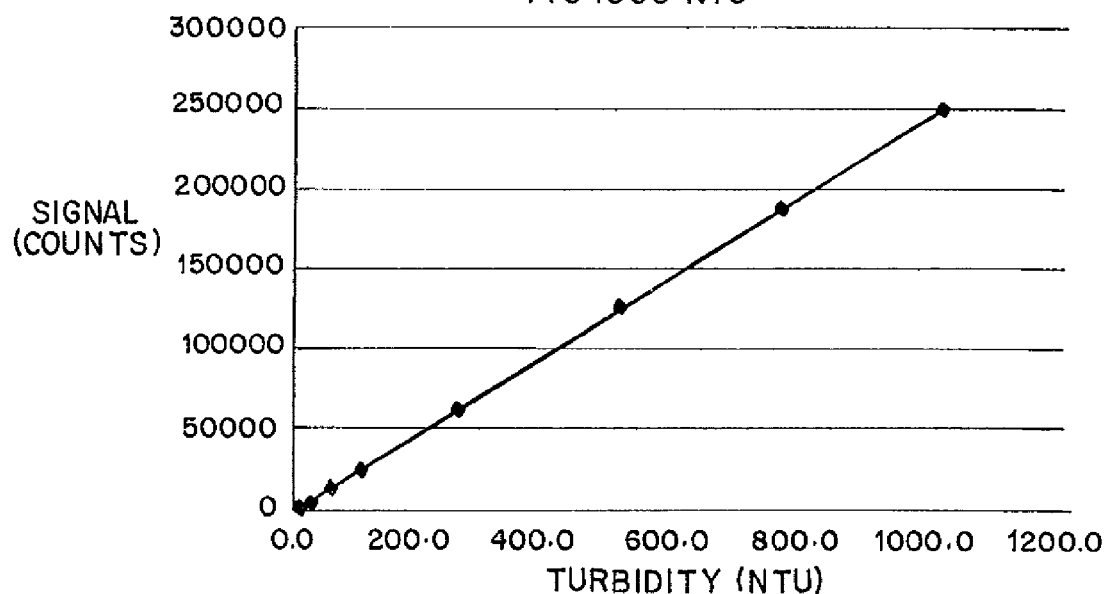
FIG. 7 is a graph of the ratiometric laser pulse turbidity response in the 1 to 1000 NTU range.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

A system designed to measure the turbidity of fluids in a closed fluid system by using a pre-calibrated disposable flowcell assembly 100 containing an in-line optical bench and a sensor assembly 120 is shown in FIG. 1. The flowcell assembly is generally designated as 100. The assembly 100 is designed to be integrable with a fluid circuit and to be disposable. Contained with the flowcell assembly 100 is a short tubular fluid conduit 102 surrounded by a cover 104.

The fluid conduit 102 is molded and designed for passing a fluid through its interior at a particular manifold flow rate range. It is intended to be connected to a fluid circuit or processing system, though it may have other uses. The tubing material of the fluid conduit 102 should be suitable for engaging and containing the fluid being handled, such as valuable proteins, protein systems, cells, cell systems, biotechnical compositions or pharmaceutical solutions. The fluid conduit 102 has molded-in fluid-tight connections such as inlet 106 at a first end and outlet 108 at a second end, which may consist of Luer, Barb, Triclover, or any connection method suitable to sealingly connect the fluid conduit 102 to a fluid-containing component in a processing system or fluid circuit such as those identified herein.

The underside of the flowcell assembly 100 mates to the reusable sensor assembly 120. The reusable sensor assembly 120 includes barbed bolts 122 and 124, which when mated to the flowcell assembly 100, are inserted through its underside. The illustrated flowcell assembly 100 is then secured by means of a rotating, locking action by which the barbed bolts releasably engage to connect together the flowcell assembly and the reusable sensor assembly.

The reusable sensor assembly 120 is connectable to a readout device, computer, processor, sensor monitor, or user interface via connection port 126. The reusable sensor assembly 120 includes sensor-specific circuitry, which also includes a gamma-stable, non-volatile memory device, chip or an EEPROM. The circuitry and non-volatile memory are accessible through the connection port 126. The non-volatile memory chip or EEPROM is used to store sensor-specific information. The non-volatile memory device associated with the reusable sensor assembly 120 stores the subassembly identity information, calibration values, calibration factors and calibration date as well as the performance characteristics of the sensor assembly 120. This information can be called up, displayed and printed out, on demand, by a readout device, processor, computer, sensor monitor, or user interface connected to the connection port 126.

The sensor assembly 120 also connects to a second non-volatile memory device, chip or EEPROM located within the flowcell assembly 100. When the flowcell assembly 100 and sensor assembly 120 are mated, the second volatile memory device is connected to sensor circuitry via electrical contacts 128. The second non-volatile memory device contains data, such as calibration values, calibration factors, performance characteristics, flowcell identification information and factory calibration data. When the flow cell is engaged, i.e. connected to the sensor assembly 120, the stored flowcell data is accessible through the circuitry of the sensor assembly 120 and is downloadable by any connected readout device, computer, sensor monitor, or user interface via connection port 126. Barcode, RFID or wireless technology also could be utilized for information handling.

The sensor assembly 120 includes apertures that are sealed against fluid transfer while allowing passage of electromagnetic radiation therethrough, such as the illustrated windows 130 and 132. When the sensor assembly 120 is mated to the flowcell 100 such as by respective docking ports, the illustrated aperture windows align with aperture plates located on the underside of the flowcell assembly 100. A energy beam source, such as LED, laser or other source of electromagnetic radiation is positioned directly below aperture window 130, within the sensor assembly 120.

Positioned below illustrated aperture window 132 is a reference photo detector. The reference photo detector is sensitive to the electromagnetic radiation produced by the energy beam source of this embodiment. Located between the aperture windows 130 and 132 is on optical window 134 in this embodiment. As shown in FIG. 2, a photo detector resides underneath the optical window 134.

FIG. 2 shows exploded views of the disposable flowcell assembly 100 and the reusable sensor assembly 120. The flowcell assembly 100 has a housing comprised of a cover 210 which sealingly and securely mates to the flowcell base 220. Connected to the flowcell base of this embodiment is a fluid conduit tube 102, with molded-in fluid-tight connections 106 and 108. The inner wall surfaces of the fluid conduit tube 102 are part of the sensor solution interface. For optimal sensor response, the inner wall surfaces of the flow-through sensor can have a mirror-like, reflective surface finish. The fluid conduit tube 102 also includes openings for the optical components.

The optical components illustrated in this embodiment comprise two reflective components that fold or change the direction of an electromagnetic radiation beam. These can be considered to be fold mirrors 222 and 224 that can be molded members with appropriately shaped reflectors. Another optical component of this embodiment is a scattered light detection window 226. The optical components can be molded from optically transparent plastic. The optical components typically are mechanically integrated (e.g. glued) into the fluid conduit tube 102, usually also a plastic or polymer. Mechanically integrating the optical components into the liquid-carrying sensor tube provides a physical separation between the fluid and the active electro-optical sensor components and maintains a hermetically sealed sensor-solution interface. When mechanically integrated, the optical components are optically isolated and surrounded by opaque material, such as molded or extruded polymeric material, in order to minimize undesirable background light scattering.

Two reflective components or fold mirrors are shown, one being an originating fold mirror 222 and the other a receiving fold mirror 224. Each fold mirror has a reflective surface, a fluid-contacting surface, and a detector surface side. The reflective surface can be made of a suitable material such as gold, aluminum, silver, nickel or alloys or combinations thereof, or polymers that contain such materials or are otherwise reflective. The fold mirrors 222 and 224 and the scattered light window 226 form an optical bench or bench module in its most elemental form. When integrated with the fluid conduit 102, the fold mirrors 222 and 224 as well as one side of the scattered light window 226 are oriented toward the inside of the tube 102 and are in contact with the solution contained within the tube 102. The scattered light window has ridge 227, which is in direct contact with the interior of the fluid conduit 102 when the window is integrated.

The scattered light window 226 and the fold mirrors are non-circumferential (i.e. they do not extend around the full circumference of the fluid conduit 102). Typically these optical bench components, and usually the entirety of the optical bench, do not extend greater than half of the circumference of the fluid container (conduit in this embodiment). For example, in FIG. 3, the optical bench extends for about one third of the circumference of the conduit.

In this embodiment, the fold mirrors 222 and 224 and scattered light detector window 226 are integrated into the plastic fluid conduit tube 102 in an aligned, collinear, longitudinal orientation. The longitudinal orientation the fold mirrors 222 and 224 and the separation of electro-optical components (light source and detectors) contained within sensor assembly 120 results in an optical path that is independent of any fluid conduit dimensions. This arrangement allows for an easy physical separation of light source and detectors and the liquid-carrying conduit. Thus, dimensional scale-up of fluid conduits is readily achieved without changing the optical path dimensions. For example, the same dimensioned optical bench can be incorporated into a ⅛" diameter or a 1.0" diameter fluid conduit or into the walls of a 20 liter bioreactor bag while obtaining the same signal, such as a turbidity signal, for a given solution.

Aperture plates 228 and 230 are located in the flowcell assembly 100 sealed below the respective fold mirrors 222 and 224. The aperture plates 228 and 230 optically isolate the fold mirrors 222 and 224. The aperture plates 228 and 230 each contain a minute aperture 232 and 234 to allow the energy beam, laser, or the electromagnetic radiation generated by the source within the sensor assembly, to pass. When the flowcell assembly 100 and the sensor assembly 120 are mated, aperture 232 located in the aperture plate 228 is positioned above and in optical alignment with the energy beam source contained within the sensor assembly 120. Similarly, aperture 234 in aperture plate 230 is positioned above the reference photo detector, when the flowcell assembly 100 and sensor assembly 120 are mated.

As stated above, the flowcell assembly 100 also includes a memory device, such as a gamma-stable, non-volatile memory device, a chip or an EEPROM, for example, which memory device is connected to a printed circuit board 236. The printed circuit board 236 is located within the flowcell assembly 120. The non-volatile memory device on the printed circuit board 236 contains data associated with the single-use, disposable flowcell 100, as stated above.

When the flowcell assembly 120 is engaged with, typically by being sealed to, the sensor assembly 120, the printed circuit board 236 electrically connects to the electrical contacts 128. As stated above, when the flowcell is connected to the sensor assembly 120, the stored flowcell data is accessible through the circuitry of the sensor assembly 120 and is downloadable by any connected (hardwire or wireless) readout device, processor, computer, sensor monitor, or user interface via connection port 126.

When the flowcell assembly 100 and the sensor assembly 120 are mated, aperture plates 228 and 230 optically align with the aperture windows 130 and 132, and the scattered light detector window 226 optically aligns with the detector window 134. The aperture windows 130 and 132 and detector window 134 are located on top cover 238 of the sensor assembly 120.

The connection port 126 is electrically connected to the printed circuit board and the components thereon. A energy beam source 244, such as LED, laser or other source of electromagnetic radiation is surface mounted onto the flat printed circuit board 242. In one embodiment, a laser diode which produces a light with the wavelength of approximately 660 nm is utilized. The operational pulse frequency of a laser diode ranges from 1 Hz to 10 kHz. The laser pulse width may range from 10 seconds to 1 microsecond, and the laser pulse height in terms of current ranges from 10 milliampere to 1.0 ampere. In the embodiment which utilizes the laser diode at 660 nm, 180 Hz is the preferred pulse frequency, 10 milliseconds is the preferred pulse width, and 0.5 ampere is the preferred pulse height current. In another embodiment the energy beam source generates ultraviolet light with a wavelength of approximately 280 nm. In this alternative embodiment, the energy beam source 244 is an ultraviolet diode with a hemispherical lens arrangement such as those sold by Sensor Electronic Technology Inc. (UV-TOP280, TO39FW). The preferred ultraviolet diode has a high optical power output in the 400 to 800 micro-Watts (uW) range and a narrow viewing angle, preferably <10°.

A photo detector 246 and a reference detector 248 are also surface mounted onto the flat printed circuit board 242. The scattered light photo diode detector 246 and reference diode detector 248 may be arranged collinearly with the light source 244, and same are sensitive to and can measure the light or electromagnetic radiation generated by the energy beam source 244. The surfaces of the scattered light photo diode detector 246 and reference diode detector 248 are aligned at an angle of approximately 90 degrees from the energy beam originating from the energy beam source 242.

All electro-optical components are surface-mounted onto a flat sensor printed circuit board 242. In this embodiment, the component side of the printed circuit board 242 is fastened to a molded plastic enclosure top cover 238, the molded plastic enclosure top cover 238 with separate cavities accommodating the energy beam source 244 with a collimating lens as well as scattered light photo diode detectors 246 and reference photo diode detector 248. The top cover 238 attaches to the bottom sealing cover 240, securing the printed circuit board 242 safely between the two.

The sensor circuitry within the printed circuit board 242 or within a connectable readout device, processor, computer, user interface, etc. provides a means of automatically interrupting the laser operation when the attached flowcell assembly 100 is disengaged from the sensor assembly 120. This is an important safety feature to prevent eye injuries, for example, during removal of the disposable flowcell 100.

FIG. 3 shows longitudinal cross-sectional view of a flowcell assembly with disposable fluid conduit tube 302 mated to a reusable sensor assembly 304. The disposable fluid conduit tube 302 has an interior surface 303 and an exterior surface 305. The interior surface may have a mirrored or reflective coating.

The reusable sensor assembly has a housing 306 which protects the printed circuit board 308. An energy beam source 310, which may be a laser diode, LED, or other source of electromagnetic radiation is surface-mounted onto the flat printed circuit board 308. One or more photo diode detectors 312a, 312b, and 312c and a reference photo diode detector 314 are also surface mounted onto the flat printed circuit board 308. The housing 310 includes a cavity formed by walls 316a and 316b, which optically isolate the energy beam source 310 from the other components. Similarly, walls 318a and 318b optically isolate the photo diode reference detector 314 from the other components.

The housing may also include cavities 320a and 320b which accommodate fold mirrors 322 and 324. The tabs 326 and 328 located on the underside of the fold mirrors 322 and 324 fit into these cavities 320a and 320b. The tabs 326 and 328 properly align the disposable fluid conduit with the reusable sensor assembly.

The fold mirrors 322 and 324 and the scattered light detector window 330 may be manufactured from any material suitable for the optical transmission of electromagnetic radiation and which may withstand sterilization. The preferred material is TOPAS®, a cyclic olefin copolymer, with refractive index of 1.53. The polymer is optically transparent from UV to the near IR wavelength range. The use of TOPAS® polymer allows low-cost mass-production and easy integration into disposable, plastic sensor tubes, bags or plastic hard-shell containers.

The fold mirrors 322 and 324 and the optical detector window 330 are integrated into their respective recesses or cavities in the disposable fluid conduit tube 302. The cavities that accommodate the optical fold mirrors 322 and 324 and detector window 330 are molded into the disposable sensor tube and provide mechanical alignment with respect to the optic-electronic detector components. The fold mirrors 322 and 324 and the scattered light detector window 330 may be glued into recesses in the disposable fluid conduit tube 302. Gluing the optical components into the liquid-carrying sensor tube provides a physical separation between the fluid and the active electro-optical sensor components and maintains a hermetically sealed sensor-solution interface. The precision of the mechanical alignment of the fold mirrors 322 and 324 and the optical detector window 330 is of critical importance for any analytical, light-based measurements, for example transmittance, absorbance, reflectance, light scattering or fluorescence.

In this embodiment, the fold mirrors 322 and 324 are separated and optically isolated from the scattered light detector window 330 by light blocks 332 and 334. Light blocks 332 and 334 are opaque plastic material, which prevents the transmission of electromagnetic radiation.

A beam 336 of electromagnetic radiation is generated by the beam source 310. The energy beam 336 may be further focused, such as by a lens 338, before passing though an aperture disk or aperture plate 340. The aperture disk 340 includes a small aperture through which the beam 336 passes, which aperture limits the diameter of the beam 336 and, thus, limits the amount of light or other energy beam which passes. The aperture disk 340 provides a consistent diameter beam 336 to provide control in that beam sources within a production lot may slightly differ. The energy beam source 310, lens 338, and aperture disk 340 are held in place and aligned by an optical alignment bezel 342 in this illustrated embodiment.

The beam 336 generated by energy beam source 310 is oriented vertically. The beam 336, after passing though the lens 338 and aperture disk 340, enters through receiving window 344 of fold mirror 322 and is reflected off the mirror-coated reflective surface 346. In order to avoid refractive light or energy beam losses and undesired scattering, the embodiment shown in FIG. 3 relies on two, opposing fold mirrors 322 and 324 with internal, mirror-coated reflector surfaces 346 and 350, respectively. The mirror-coating 348 is a material sufficient to reflect electromagnetic radiation, such as gold. The fold mirrors 322 and 324 extend within the fluid conduit 302. As a result, the angled reflective surfaces 346 and 350 of the fold mirrors 322 and 324 (and the optical bench) are located within the interior of the fluid conduit tube 302 and extend toward the longitudinal axis of the fluid conduit 302.

The optical light path is further illustrated in FIG. 3A. As shown in FIG. 3A, angle "p" (beta) between the vertical energy beam 336 generated by the vertically positioned energy beam source 310 and the normal (illustrated at 364) of the reflector surface is less than or equal to a critical angle, typically 45 degrees. The energy beam 336 is reflected off the internal, mirror-coated reflective surface 346 and travels at an approximately 90 degree angle from its originating vector. The angle may vary so as to account for the refractive indexes of the material used (including of the windows) and the fluid contained within the fluid conduit 302. The energy beam 336 exits the fold mirror through the emitting reflector window 352 on the fluid-contacting side of the fold mirror 322.

On the fluid-contacting side of the fold mirrors, the reflected laser beam transverses a path generally parallel to an optically transparent scattered light window 330. The scattered light window is located between and below the emitting reflector window 352 and the receiving reflector window 354 of fold mirror 322 and 324, respectively. On the fluid-contacting surface of the fold mirrors, the emitting reflector window 352 radiates a high-intensity, collimated energy beam 336 parallel to the inside (longitudinal) fluid conduit tube 302 surface and parallel to the scattered light window 330. In the case of flow through sensor designs, the inner wall surfaces are part of the sensor solution interface.

On the fluid-contacting side of the fold mirrors 322 and 324, the emitting reflector window 352 as well as the receiving reflector window 354 oppose each other and are oriented at approximately 90 degrees with respect to the energy beam 336 as the originating energy beam 336 transverses through the fluid conduit 302. The orientation angle may vary given the respective refractive indices of the fluid and of the fold mirrors 322 and 324.

As the energy beam 336 travels though the fluid contained within the fluid conduit tube 302, it may strike and be scattered by particulate matter within the fluid. This scattered energy beam or light 356 (represented by arrows) may then pass through the scattered light detector window 330 and be detected and measured by one or more photo detectors 312a, 312b, and 312c.

That portion of beam 336 that travels unabated, unimpeded, or un-reflected through the fluid passes through the receiving reflector window 354 of fold mirror 324. The energy beam 336 is reflected approximately 90 degrees downward by the internal, mirror-coated reflector surface 350, which as an acute angle with respect to the energy beam path. The mirror-coated reflector surface 350 has a surface normal to it, as illustrated at 366 in FIG. 3A. The angle "δ" (delta) between the energy beam 336 and the normal 366 is less than or equal to a critical angle, typically 45 degrees. The mirror-coating 358 which creates mirror-coated reflector surface 350 is a material sufficient to reflect electromagnetic radiation, such as gold.

The reflected beam 336 travels downward through the exiting window 360 of the fold mirror 324. The remaining portion of the beam 336 is directed towards reference photo detector 314. The reference photo detector 314 monitors the transmitted laser light or energy beam and acts as a reference detector, i.e. it detects and measures the intensity of the beam 336 that traveled unabated through the fluid conduit tube 302.

The analytical signal, derived from the detected scattered energy beams or light 356 (represented by arrows) of suspended solution particulates, is generated within the space defined by the diameter of the beam 336 as it transverses the fluid conduit 302 and the distance between the two, opposing emitting reflector window 352 and receiving reflector window 354. The embodiment shown in FIG. 3 also allows monitoring the outputs of either scattered energy beam or light detectors 312a, 312b, and 312c or the output of the reference photo detector 314 or the signal ratio of (scattered light detector/reference detector). The ratio-metric approach provides a means for removing the effects of solution color and/or protein adsorption on any of the windows of the optical bench (e.g. the scatter light window 330). Monitoring of the output of one or more of the scattered light detectors 312a, 312b, and 312c and the output of the reference photo detector 314 cancels any interference present in the measurement, as it is understood that the scattered light detectors 312a, 312b, and 312c and reference photo detector 314 are equally affected.

Sensor circuitry, located on the printed circuit board 308, or in a connectable readout device, processor, computer, user interface, etc. allows measurement of photo detector dark currents between laser pulses. The photo detector current measured during the laser pulse minus the photo detector dark current measured between pulses constitutes the analytical turbidity signal.

The longitudinal fold mirror orientation within the fluid conduit tube 302 and separation of electro-optical components by the energy beam source and photo detectors generates an optical path that is independent of any dimensions of the fluid conduit tube 302. This arrangement allows for an easy physical separation of energy beam source and detectors on one hand and the liquid-carrying conduit on the other hand. Thus, scale-up of conduit dimensions are readily achieved without changing the optical path dimensions. The same dimensioned optical bench can be incorporated into differently sized systems. For example, the same optical bench dimensions can be used with a range of fluid container sizes, such as a ⅛" diameter, a 1.0" diameter (or intermediate or other-sized diameter) liquid conduit or into the walls of a bioreactor bag, while obtaining the same signal for a given calibration solution, such as a turbidity calibration solution.

The optical path of the energy beam 336 of this embodiment originates at the energy beam source 310. The optical beam flows in a straight path or line through a lens 338 and through an aperture disk 340, and enters through the first surface of a first member of the optical bench or bench module, the receiving window 344 of fold mirror 322.

The optical path is then reflected off a second surface, the reflective surface 346 or the first member, of the optical bench. This second surface, the reflective surface 346, has an acute angle relative to this first surface, the receiving window 344. The optical path exits out of the first fold mirror 322 through a third surface of the first member, emitting reflector window 352. The scattered light window 330 is located below reflective surfaces 346 and 356. As a result, the optical path travels through the fluid conduit tube 302, above the upper surface 362 of the scatter light window 330. In this illustrated embodiment, the optical path is generally parallel to the upper surface of the scatter light window 330.

The optical path in this embodiment continues to a second member, through its fourth surface, receiving reflector window 354 of the second fold mirror 324. The third surface and this fourth surface substantially oppose each other. A fifth surface of the second member, reflective surface 358, reflects the optical path downward through a sixth surface of the second member, the exiting window 360 of the fold mirror 324. This fifth surface, the reflective surface 356, has an acute angle relative to this sixth surface, the exiting window 360. The optical path concludes at a photo detector 314. The first, third, fourth, and sixth surfaces and said upper surface of the scattered light window 330 are optically transparent allowing for the transmission of electromagnetic radiation.

All critical dimensions of the optical path of the energy beam 336 are stable and fixed. Collimated energy beam 336 traces are well defined and can be reproducibly generated. This design feature allows sensor calibration and scalability. For example, for a given turbidity solution, the same optical sensor response is obtained regardless of the sensor tube diameter or the container size.

FIG. 4 shows another embodiment of the present invention. The embodiment shown in FIG. 4 demonstrates modifications to the embodiment presented in FIG. 3. Some or all modifications may be practiced. These include that the optical bench 402 may be a unitary piece. Also, the originating vector of energy beam 404 may be angled rather than generally perpendicular with respect to the conduit tube and/or scattered light window, with the result that the reflection angle is greater than 90° or obtuse. In another variation, the reflective surfaces 406 and 408 of the optical bench are non-mirrored surfaces, i.e. have no mirrored coating.

The optical bench 402 as shown in FIG. 4 is a unitary piece without separate components. Such an optical bench may include in its unitary construction light blocks to prevent the transmission of light through unintended areas of the optical bench 402. This optical bench embodiment includes entrance window 412, an emitting window 414, a receiving window 416, and an exit window 418. The emitting window 414 and receiving window 416 are located on the fluid-contacting side of the optical bench. The emitting window 414 and receiving window 416 are opposing, facing windows. Located between the emitting window 414 and the receiving window 416 is the scattered light window 420. The optical bench 402 may be made of any material which permits the transmission of electromagnetic radiation, such as a beam of infra-red (IR) or ultra-violet (UV) light.

Optical bench 402 of this embodiment is integrated with a disposable fluid conduit tube 422. The fluid conduit tube 402 is shown in FIG. 4 attached to the reusable sensor assembly 424. Reusable sensor assembly 424 includes a printed circuit board 426 on which electro-optical components are mounted. A energy beam source 428, which may be a laser diode, LED, or other source of electromagnetic radiation, is mounted onto the flat printed circuit board 426. The energy beam source 428 may be mounted at an angle other than 90° such that the energy beam 404 originates at an angle other than 90° with respect to the printed circuit board. It is also contemplated that the energy beam 404 may be angled in this sense by means of a mirrored surface contained within the reusable sensor assembly 424.

Adjacent the energy beam source 428 is a lens 430. Located along the optical path from the lens 430 is an aperture disk 432. The energy beam source 428, lens 430 and aperture disk 432 are held in optical alignment by an optical alignment bezel 434 or the like.

One or more scattered light photo diode detectors 436a, 436b, and 436c are mounted on the printed circuit board 426. A reference photo diode detector 438 is also mounted to the printed circuit board 426. The scattered light photo diode detectors 436a, 436b, and 436c, reference photo diode detector 438, and the energy beam source 428 are collinearly arranged on the printed circuit board 426.

Optically opaque walls 440 and 442 of the sensor assembly 424 separate the components. The scattered light photo diode detectors 436a, 436b and 436c are separated from the energy beam source 428 by opaque wall 440. Likewise, the scattered light photo diode detectors 436a, 436b and 436c are separated from the reference photo diode detector 438 by opaque wall 442. The opaque walls insolate the components, especially the detectors, from unintended electromagnetic radiation.

The optical path of the energy beam 404 originates at the energy beam source 428. The originating vector of the energy beam 404 is angled, though it is contemplated that the energy beam 404 may be "bent" angled via a mirrored surface contained within the sensor assembly 424. The energy beam 404 travels though a focusing lens 430 and aperture disk 432. The aperture disk 432 includes a small aperture which limits the diameter of the energy beam 404. The energy beam 404 enters the optical bench through entrance window 412 and is reflected off the reflective surface 406.

The reflective surfaces 406 and 408 use the refractive properties of the material used from which the optic bench 402 is constructed and the fluid components contained with the fluid conduit tube 402 that reflect the electromagnetic radiation. As shown in FIG. 4A, the angles "θ" (theta) and "φ" (phi) between the energy beam 404 and the normal 446 of reflector surface 406 and the normal 448 of reflector surface 408 is greater than or equal to a critical angle. The critical angle of the reflective surfaces 406 and 408 is defined by: αc=arcsin (n1/n2), where n1 is index of refraction of the solution (1.33 for water) and n2 is the index of refraction of the optical reflector material (1.53 for TOPAS®, COC). For example, a water-TOPAS® reflector interface, the critical angle is approximately 57°. For any angle of "θ" and "φ" which is greater than or equal to 57° the energy beam 404 is totally reflected at the internal reflector surface 406 or 408. If the angle is less than 57° the energy beam is partially refracted through the internal reflector surface and constitutes an undesirable optical background scatter.

On the detector side of the optical arrangement, a beam entrance window 412 is located approximately 90°, or normal to the optical axis of the energy beam 404 that originates from the energy beam source 428 (i.e. a laser diode in this embodiment) and associated aperture of the aperture disk 432. The optical beam axis intersects with the normal of the internal reflector surface at an angle that is equal or larger than the critical angle, ac.

The incident energy beam 404 is reflected from the internal reflector surface 406 making an angle "θ" (with respect to the normal 446 of sloped reflector surface 404) that is defined by φ≥αc=arcsin (n1/n2), as defined above. Once reflected, the energy beam 404 travels through the emitting window 414 located on the fluid-contacting side of the optical bench 402. The energy beam 404 then travels through a fluid contained within the fluid conduit tube 422. As it travels through the fluid, the energy beam 404 is scattered by particles in the fluid. This scattered light 440 (represented by arrows) may travel through the scattered light window 420 of the optical bench 402. The scattered light 440 strikes and is measured by one or more of the scattered light photo detectors 436a, 436b, and 436c.

The portion of energy beam 404 that travels unabated, unimpeded, or un-reflected through the fluid passes through the receiving reflector window 416. The energy beam 404 is then reflected by internal reflector surface 408 making an angle "φ" (with respect to the normal 448 of sloped reflector surface 408) that is defined by θ≥αc=arcsin(n1/n2), as defined above. Once reflected, the energy beam travels through the exiting window 418 located on the detector side of the optical bench 402. After exiting the inset optical component or optical bench 402, the energy beam 404 strikes reference detector 438 and is measured there by the reference detector 438.

The analytical signal, derived from the detected scattered light 444 (represented by arrows) of suspended solution particulates, is generated within the space defined by the diameter of the energy beam 404 as it transverses the fluid conduit 422 and the distance between the two, opposing emitting reflector window 414 and receiving reflector window 416. The embodiment shown in FIG. 4 also allows monitoring the outputs of either scattered light detectors 436a, 436b, and 436c or the output of the reference photo detector 438 or the signal ratio of (scattered light detector/reference detector). The ratio-metric approach provides a means for removing the effects of solution color and/or protein adsorption on any of the windows of the optical bench (e.g. the scatter light window 420).

FIG. 5 shows another embodiment of the present invention and demonstrates possible modifications to the embodiments presented in FIG. 3 and FIG. 4. As shown in FIG. 5, in this embodiment, the optical bench has only one internal reflector. The optical bench does not include a receiving window, a second internal reflector, or an exit window. Additionally, the sensor assembly 506 of this embodiment does not necessarily include a reference detector. It is contemplated that the sensor assemblies as shown in the embodiments of FIG. 3 and FIG. 4 may be connected to the optical bench in FIG. 5; however, the reference detector is turned off or is not utilized when such a connection is made. The embodiment having a single internal reflector, as demonstrated in FIG. 5, is particularly useful for very low NTU turbidity measurements.

The optical bench in FIG. 5 comprises a fold mirror 502 and a scatter light detector window 504 integrated within a disposable fluid conduit tube 506. The fold mirror 502 and the scattered light window 504 are made of any material which permits the transmission of electromagnetic radiation, such as a beam of light.

Located between the fold mirror 502 and the scattered light window 504 is a light block 508. The light block 508 is made of opaque material and prevents the inadvertent transmission of electromagnetic radiation. A second light block 510 may be located on the opposite side of the scattered light window 504. The second light block may be made of opaque material and prevents the inadvertent transmission of electromagnetic radiation through to the components of the reusable sensor assembly 512.

In this embodiment, the fold mirror 502 includes an internal, mirror-coated reflector surface 514. The mirror-coating material 516 is any material that can reflect electromagnetic radiation, such as those discussed herein. A non-mirror-coated reflector surface may also be used as described above. The fold mirror 502 also includes an entrance window 518 and an emitting window 520.

The disposable fluid conduit tube 506 is removably attached to the reusable sensor assembly 512. The reusable sensor assembly includes a printed circuit board 520. Mounted on the circuit board are one or more scattered light photo diode detectors 522a, 522b, and 522c and a energy beam source 524, which may be a laser diode, LED, or other source of electromagnetic radiation. The scattered light photo diode detectors 522a, 522b, and 522c and a energy beam source 424 may be collinearly arranged on the printed circuit board.

The energy beam source 524 generates a energy beam 526 of electromagnetic radiation. The energy beam 526 travels through a lens 528 which focuses the energy beam 526. Thereafter, the energy beam 526 passes through an aperture disk 528. The aperture disk 528 has a small aperture which limits the diameter of the energy beam 526. The energy beam 526 then pass through the entrance window 518 of fold mirror 502. After entering the fold mirror 502, the energy beam is reflected off of the internal, mirror-coated reflector surface 514. The energy beam then passes out of the fold mirror 502, through the emitting window 520 and into the fluid contained within the fluid conduit tube 506. The energy beam 506 may encounter suspended particles in the fluid, which creates scattered energy beams 530 (represented by arrows). The energy beam 506 continues indefinitely through the fluid conduit tube.

The scattered energy beams 530 may pass through the scattered light window 504 of the optical bench of this embodiment. Thereafter, the scattered energy beams 530 strike and are measured by one or more of the scattered light photo detectors 522a, 522b and 522c.

FIG. 6 shows an embodiment having optical bench or optical inset component 602 integrated into a disposable bioreactor bag and removably attached to a reusable sensor assembly 606 which houses the electro-optical components, similar to the other illustrated embodiments. The disposable bioreactor bag 604 includes an access port 608 which may be connected to a fluid circuit, tubing, etc. The interior of the disposable bioreactor bag 604 may include a solution 610 having suspended particles and possibly air 612.

Any of the aforementioned optical bench designs may be integrated with a disposable bioreactor bag 604 or other similar container. The optical bench 602 shown in FIG. 6 has a unitary design. The optical bench may include in its unitary construction light blocks to prevent the transmission of light through unintended areas of the optical bench 602. The optical bench includes entrance window 612, an emitting window 614, a receiving window 616, and an exit window 418, each window being a surface of said optical bench 602. The emitting window 614 and receiving window 616 are located on the side that is exposed to and/or contacts the optical bench. The emitting window 614 and receiving window 616 are opposing, facing windows. Located between the emitting window 614 and receiving window 616 is the scattered light window 620. The optical bench or bench module 602 may be made of any optically clear material which permits the transmission of electromagnetic radiation, such as a beam of light.

The bioreactor bag 604 is shown in FIG. 6 releasably attached to the reusable sensor assembly 606. This provides a modular approach and allows for exchange of bench modular units, much like the other illustrated embodiments. A docking port in each of the bioreactor bag 604 and the sensor assembly 606 facilitates such exchange.

The reusable sensor assembly 606 includes a printed circuit board 622 on which electro-optical components are mounted. A energy beam source 624, which may be a laser diode, LED, or other source of electromagnetic radiation, is mounted onto the flat printed circuit board 622. The energy beam source 624 is shown mounted vertically such that the energy beam 626 which originates from the energy beam source has an origination vector which is perpendicular to printed circuit board 622 and the components mounted thereon. The other components include one or more scattered light photo diode detectors 628a, 628b, and 628c and a reference photo diode detector 630. The scattered light photo diode detectors 628a, 628b, and 628c, reference photo diode detector 438, and the energy beam source 428 may be collinearly arranged on the printed circuit board 622.

Adjacent the energy beam source 624 in this embodiment is a lens 632. Located along the optical path from the lens 632 is an aperture disk 634. The energy beam source 624, lens 632 and aperture disk 634 are held in optical alignment by optical alignment bezel 636.

Optically opaque walls 638 and 640 of the sensor assembly 606 separate and optically insolate the components. The scattered light photo diode detectors 628a, 628b, and 628c are separated from the energy beam source 624 by opaque wall 438. Likewise, the scattered light photo diode detectors 628a, 628b, and 628c are separated from the reference photo diode detector 630 by opaque wall 640.

The optical path of the energy beam 626 originates at the energy beam source 624. The originating vector of the energy beam 626 is vertical, though it is contemplated that the energy beam 626 may be at another angle via a mirrored surface contained within the sensor assembly 606. The energy beam 626 travels though a focusing lens 632 and aperture disk 634. The aperture disk 634 includes a small aperture which limits the diameter of the energy beam 626.

The energy beam 626 enters the optical bench or bench module 602 through entrance window 612. The energy beam 626 is then reflected off the internal reflective surface 642 and travels at an approximately 90 degree angle from its originating vector. The angle may vary accounting for the refractive indexes of the material used and the fluid 610 contained within the bioreactor bag 604. The energy beam 626 exits the bench 602 through the emitting reflector window 614 on the fluid-contacting side of the bench 602. The energy beam 626 then travels through the fluid 610, generally parallel to the scattered light window 610. As the energy beam 626 travels through the fluid 610 it may be reflected or scattered by particles within the fluid. This scattered light (represented by arrows 644) may pass through the scattered light window 620.

The energy beam portion 626 that travels unabated, unimpeded, or un-reflected through the fluid 620 passes through the receiving reflector window 616 of fold mirror 324. The energy beam 626 is reflected approximately 90 degrees downward by the internal reflector surface 646. The reflected energy beam 626 travels downward through the exiting window 618 of the optical bench 602. The remaining portion of the energy beam 626 strikes reference photo detector 630. The reference photo detector 630 monitors the transmitted laser light and acts as a reference detector, i.e. it detects and measures the intensity of the energy beam 626 that traveled unabated through the bioreactor bag 604.

The scattered light 644 which passes through scattered light window 620 is detected and measured such as by one or more scattered light photo detectors 628a, 628b and 628c, as illustrated.

When used in the turbidity sensor context, the turbidity of the fluid 610 is determined by comparing the ratio of the measurements made by the reference detector 622 to the photo scattered light detectors 628a, 628b, and 628c.

The embodiments described herein are capable of monitoring solution turbidity in the range from 0.1 to 1000 NTU. The lower detection limit is 0.05 NTU, and associated noise level is 0.01 NTU. FIG. 7 shows the ratiometric laser pulse turbidity response in the 1.0 to 1000 NTU range when utilizing the embodiments described herein. As stated above, analytical signal, derived from the detected scattered light of suspended solution particulates, is generated within the space defined by the diameter of the energy beam 404 as it transverses the fluid conduit or bioreactor bag and the distance between the two opposing emitting reflector windows and receiving reflector window. If the receiving reflector is absent, as with some embodiments, then the signal is based on the length of the scattered light window of the optical bench.

Using the ratiometric approach, the measurements of scattered light detectors is compared against the measurements of the reference photo detector (scattered light detector/reference detector). The ratiometric approach provides a means for removing the effects of solution color and/or protein adsorption on any of the windows of the optical bench (e.g. the scatter light window 420). Testing has shown that using the ratiometric approach, the response is generally linear for a given turbidity of the solution when the turbidity is between 1 to 1000 NTU.

Figure 8:
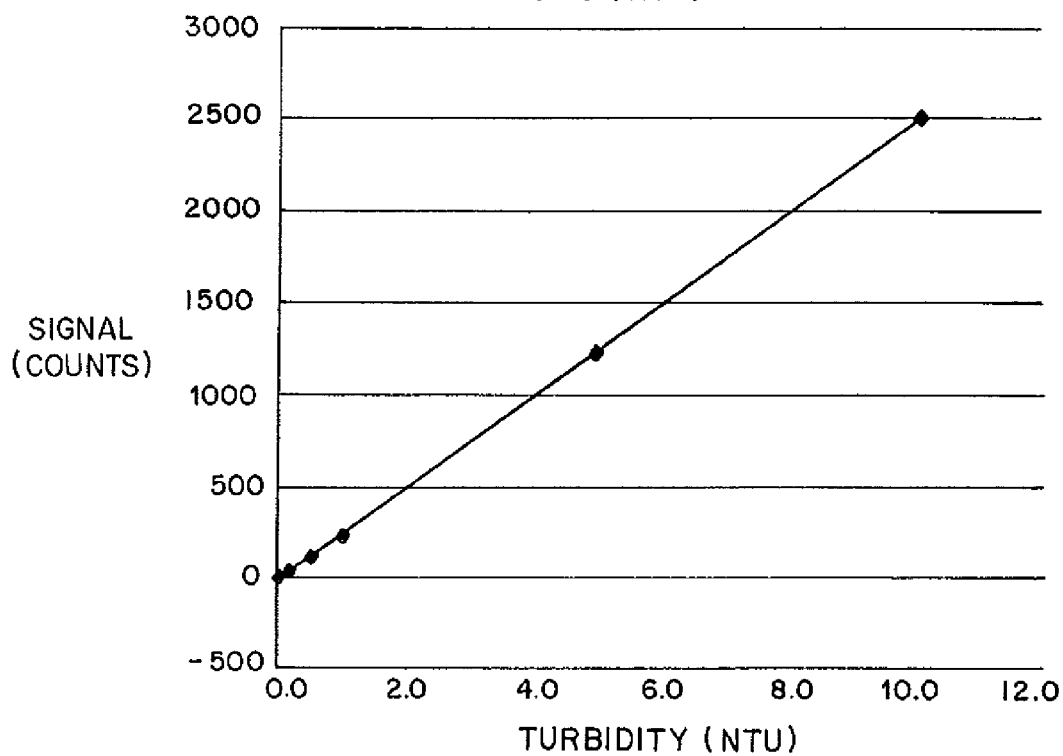
FIG. 8 is a graph of the ratiometric laser pulse turbidity response in the 0.1 to 10 NTU range.

FIG. 8 shows the ratiometric laser pulse turbidity response in the 0.1 to 10 NTU range when utilizing the embodiments described herein. Again, testing has shown that using the ratiometric approach, the response is generally linear for a given turbidity of the solution when the turbidity is between 0.1 to 10 NTU.

Sensor accuracy and precision are primarily limited by the performance specifications of the energy beam sources, photo detectors and associated electronics. The sensor accuracy is optimized through a factory calibration of the assembled sensor PCB containing the optic-electronic components, typically photo detectors and laser diode. The sensor accuracy is further optimized by calibrating the operational turbidity sensor. A NIST-traceable calibration solution of know turbidity is pumped through the operational sensor assembly during calibration. The calculated and sensor-specific calibration factor, values and zero-offset and are stored in the gamma-stable sensor memory device (such as an EEPROM or FRAM) for later recall during sensor field-use.

Figure 9:
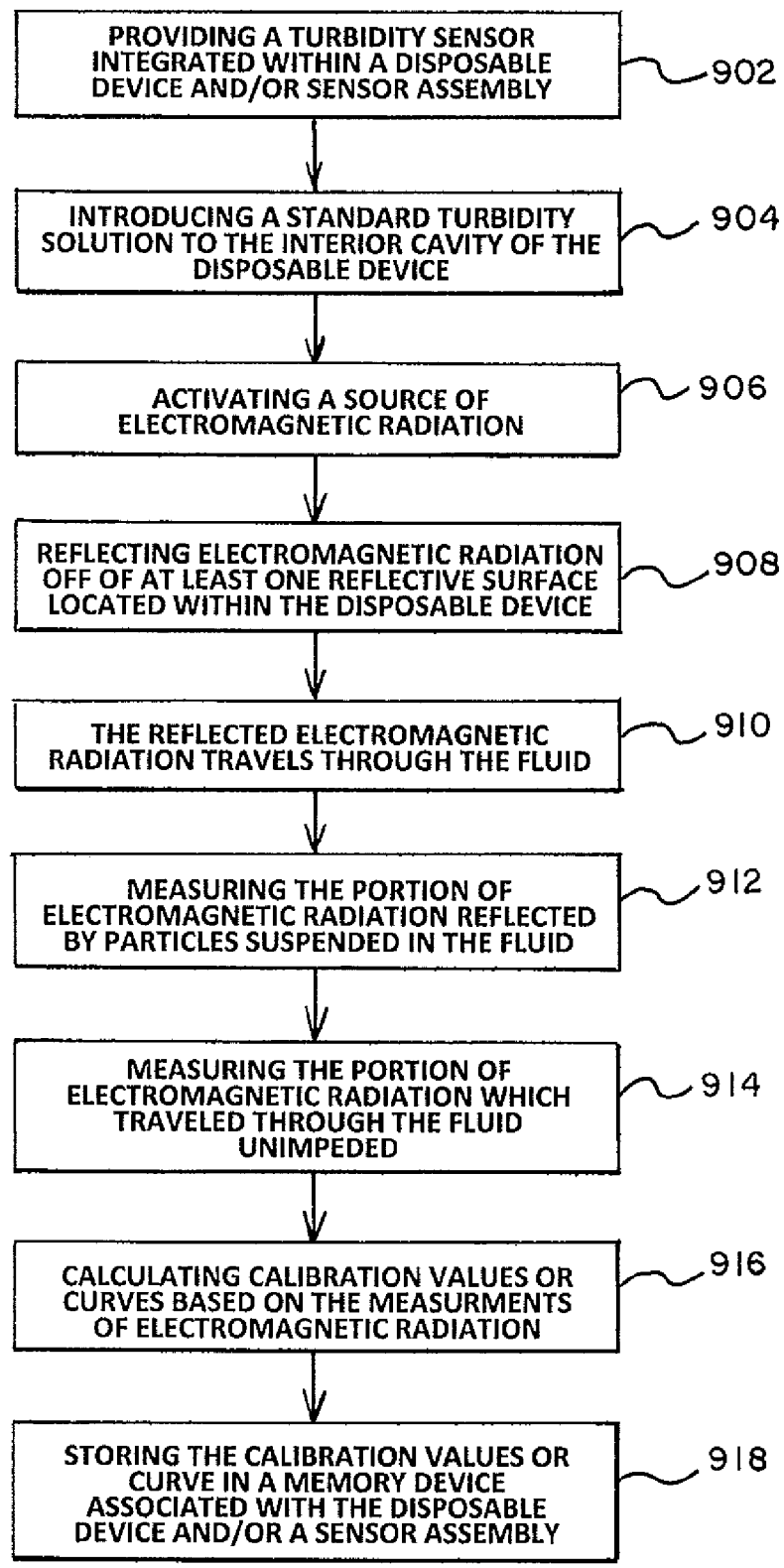
FIG. 9 is a flowchart of the steps to calibrate a disposable turbidity sensor.

The present invention also includes a method of calibrating a turbidity sensor as illustrated in FIG. 9. The sensor monitor and associated firmware allows factory calibration of the electro-optical sensor assembly, the disposable fluid conduit, disposable bioreactor bag, or disposable container, as well as the factory calibration of the complete turbidity sensor assembly and disposable fluid conduit or container mated together. NIST-traceable standard turbidity solutions are used for factory calibration. A monitor-based algorithm calculates and stores in a memory device (such as an EEPROM) a turbidity calibration curve in terms of Nepholemetric Turbidity Units (NTU) by utilizing the known value of the standard turbidity solution, the measured turbidity sensor signal taken, and taking into account the calibration data of the fluid conduit tube and the electro-optical subassembly.

In the method embodiment of FIG. 9, a disposable conduit tube or container has an inlet for receiving a fluid is provided or utilized in a first action 902. The disposable conduit tube or container may be mated to a sensor assembly as described herein. The sensor assembly has an electromagnetic radiation source as well as one or more photo detectors. The photo detectors are sensitive to and can measure the intensity of electromagnetic radiation created by the source.

A portion of the turbidity sensor is integrated within the interior cavity of a disposable conduit tube or container. The turbidity sensor includes one or more reflective surfaces. At least one of reflective surfaces of the turbidity sensor is located within the cavity of the tube or container. The reflective surfaces may be internal reflector surfaces of an optical bench as described herein.

A fluid with a known concentration of suspended particles (a standard turbidity solution) is delivered to the interior cavity through an inlet, such as an access port or end of a fluid-conduit tube in a second action 904. As a result, the fluid comes in contact with the turbidity sensor. Electromagnetic radiation, such as a energy beam or laser beam with a wavelength of 660 nm or 220 nm, is then activated as illustrated at 906. The electromagnetic radiation is reflected off of at least one of said reflective surfaces, illustrated as action 908, and thereafter the electromagnetic radiation travels through the fluid, noted at 910. At least a portion of electromagnetic radiation which is reflected by the suspended particles and is measured, noted at 912. The remaining portion of the electromagnetic radiation which passed through the fluid in an unimpeded or un-reflected condition is measured, noted at action 914.

Based on the two measurements (the portion of electromagnetic radiation which was reflected by the suspended particles and the portion of the electromagnetic radiation which passed through the fluid in an unimpeded) one or more calibration values are calculated, noted at 916. The calculation may be based on a ratiometric comparison of the portion of electromagnetic radiation which was reflected by the suspended particles and the portion of the electromagnetic radiation which passed through the fluid in an unimpeded fashion. An algorithm calculates a turbidity calibration curve in terms of Nepholemetric Turbidity Units (NTU) by utilizing the known value of the standard turbidity solution, as well as the measured turbidity sensor signals.

The calculated and sensor-specific calibration factor, calibration values and zero-offset are stored as noted at 918 in the gamma-stable sensor memory device (such as an EEPROM or FRAM) for later recall during sensor field-use. Other data, such as the calibration curve, flowcell ID, and calibration date, may also be in memory device. The memory device is associated with or contained within fluid conduit assembly or the sensor assembly as, for example, shown in FIG. 2. When the turbidity sensor is connected to a readout device, processor, computer, sensor monitor, or user interface, the stored calibration curve and other values are accessible and used to instruct readout device, computer, etc. as to the calibration as well as calibrate other associated devices.

The aforementioned embodiments include a selection of novel sensor materials, innovative circuit designs which separate the analog and digital circuits, labeling to preserve sensor-specific information, and a user interface that includes supporting software and procedures to accommodate, retrieve, interpret and calculate sensor-specific information. These materials, circuits, and labeling, are designed to withstand the conditions of the sterilization methods used by the bio-pharmaceutical industry. However, gamma or electron-beam irradiation may render a memory chip or EEPROM non-functional, and it is contemplated that the flowcell assemblies, bioreactor bags, and reusable sensor assemblies may be manufactured without a memory chip. In these embodiments, the analog components are manufactured and assembled into sensors. The sensors are validated, and the sensor specific information is then printed on the sensors or shipping bags in print, RFID or barcode form. The sensors are then placed in shipping bags or other suitable containers, irradiated via gamma rays or electron-beam, and then delivered to the user. The sensor-specific information is entered into the user interface either by a barcode scanner or the like, or manually by the user. This embodiment saves the costs associated with otherwise including the memory chip with the sensor.

The aforementioned embodiments include a selection of novel sensor materials, innovative circuit designs which separate the analog and digital circuits, labeling to preserve sensor-specific information, and a user interface that includes supporting software and procedures to accommodate, retrieve, interpret and calculate sensor-specific information. These materials, circuits, and labeling are designed to withstand the conditions of the sterilization methods used by the bio-pharmaceutical industry.

Figure 10:
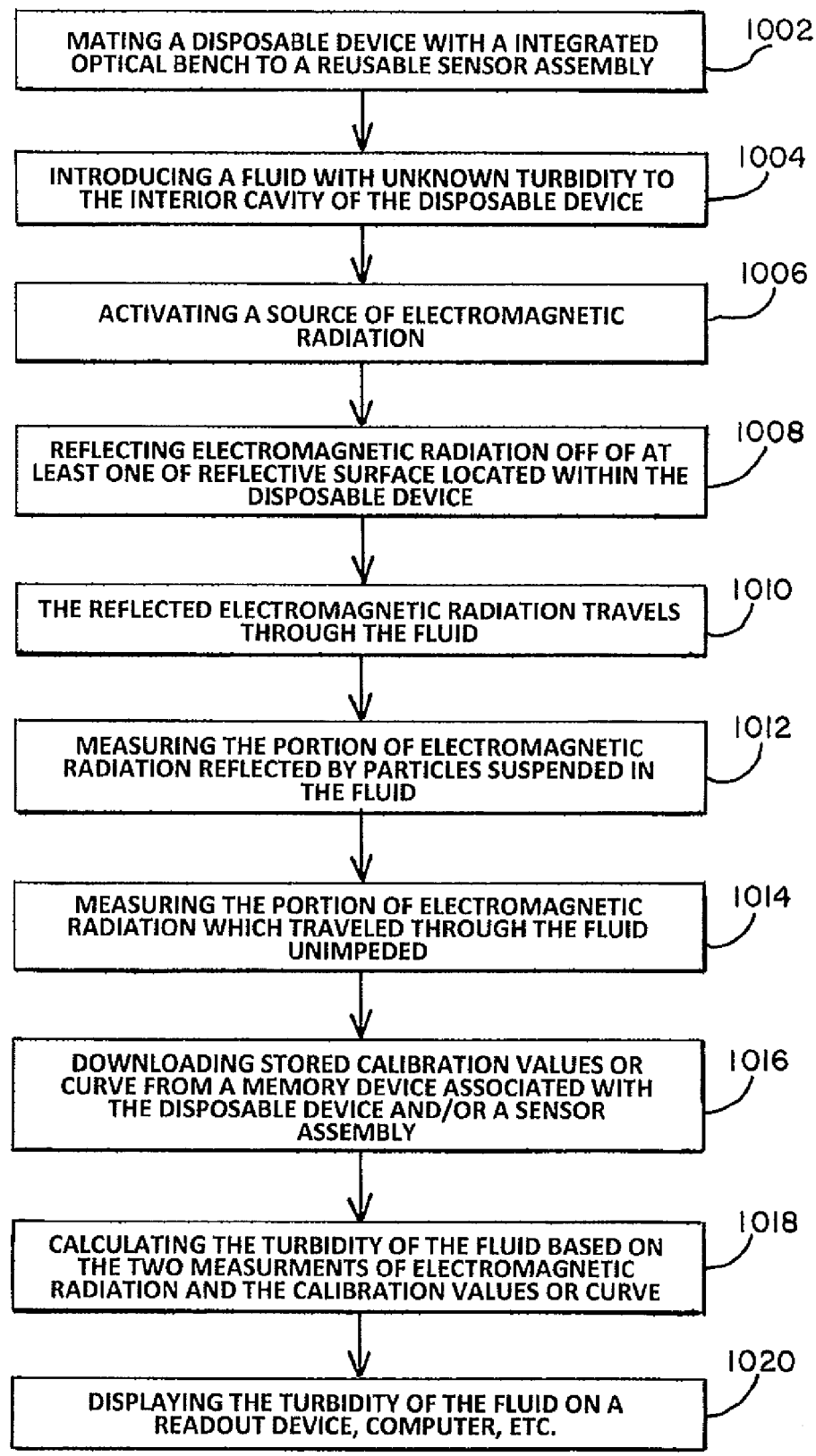
FIG. 10 is a flowchart of the steps to utilize a disposable turbidity sensor to determine the turbidity of a fluid.

As shown in FIG. 10, the present invention also includes measuring methods. FIG. 10 illustrates the method of measuring the turbidity of a fluid utilizing a disposable fluid conduit, disposable bag or container and a reusable sensor assembly. The reusable sensor assembly is connectable to a disposable fluid conduit, disposable bag or container. The reusable sensor assembly includes the disposable fluid conduit, disposable bag or container.

A disposable conduit or container is mated to a sensor assembly as shown at action summary 1002. The disposable conduit or container has an inlet and interior cavity for receiving a fluid. The disposable conduit or container also has an integrated optical bench with any of the features described above. The optical bench may be comprised of one or more reflective portions or surfaces, the reflective portions or surfaces located within the interior of the disposable conduit or container or extending toward the interior of said conduit or container.

A fluid having suspended particulates and an unknown turbidity is delivered into the interior cavity of the disposable conduit or container, noted at 1004. Electromagnetic radiation, such as a energy beam or laser beam with a wavelength of 660 nm or 220 nm, is then activated, noted at 1006. The electromagnetic radiation is reflected off of at least one of said reflective surfaces, depicted at 1008, and thereafter the electromagnetic radiation travels through the fluid as at 1010. At least a portion of electromagnetic radiation which is reflected by the suspended particles in the fluid and is measured as at 1012 by the sensor assembly. The remaining portion of the electromagnetic radiation which passed through the fluid in an unimpeded or un-reflected condition is measured as at 1114 separately by the sensor assembly.

Calibration values, such as a zero-offset, or a calibration curve based value are downloaded from a memory device associated with the disposable conduit or bag and/or the sensor assembly as at 1016. Based on the two measurements (the portion of electromagnetic radiation which was reflected by the suspended particles and the portion of the electromagnetic radiation which passed through the fluid in an unimpeded) and one or more calibrations values, the turbidity of the fluid is determined, noted at 1018. The turbidity calculation may be based on a ratiometric comparison of the portion of electromagnetic radiation which was reflected by the suspended particles and the portion of the electromagnetic radiation which passed through the fluid in an unimpeded offset by the calibration values or the calibration curve. The turbidity may then be displayed or stored by a readout device, computer, user interface, etc., as noted at 1020.

It will be understood that the embodiments of the present invention which have been described are illustrative of some of the applications of the principles of the present invention. Numerous modifications, including stated and unstated combinations of features, may be made by those skilled in the art without departing from the true spirit and scope of the invention.

The invention claimed is:

1. A sensor device employing electromagnetic radiation, comprising a sensor module and a disposable optical inset module configured to dock with the sensor module,
    said sensor module being reusable and having an electromagnetic source and a detector thereof; and
    said disposable optical inset module includes:
    (a) a cell comprising a conduit or container having an interior that contains a fluid when in use, a first member having a reflective surface and a second member having a reflective surface, said first and second reflective surfaces being at least partially within the interior of the conduit or container and able to reflect electromagnetic radiation emanating from the sensor module;
    (b) said first member reflective surface and said second member reflective surface are in substantial optical alignment with each other, whereby electromagnetic radiation originating from the sensor module, when docked with the disposable optical inset module, is reflected off said first member reflective surface, travels to and then is reflected off one or more particulates of the fluid or travels to and then is reflected off said second member reflective surface; and
    (c) a third member having a surface that permits transmission therethrough of electromagnetic radiation reflected off one or more particulates of the fluid, said third member surface being disposed between said first member surface and said second member surface, said third member surface being substantially parallel to the travel of electromagnetic radiation between the first member and second member surfaces.

2. The sensor device of claim 1, wherein the sensor device is a turbidity sensor.

3. The sensor device of claim 1, wherein said first member and second member have respective reflective surfaces with a mirrored coating of material suitable to reflect electromagnetic radiation.

4. The sensor device of claim 1, wherein said first member and said second member reflective surfaces comprise a material that reflects electromagnetic radiation, the material selected from the group consisting of gold, aluminum, silver, nickel, combinations thereof, alloys thereof and polymers containing same.

5. The sensor device of claim 1, wherein said third member surface is an optically clear material.

6. The sensor device of claim 1, wherein the first member and the second member extend beyond the third member and electromagnetic radiation reflects off objects between the first and second members.

7. The sensor device of claim 1, wherein said disposable cell comprises:
(a) a molded fluid conduit tube having first and second ends and an interior for passing a fluid therebetween, said tube having the third member surface that is an optically clear portion that extends less than the full circumference of the tube;
i) said first member reflective surface and said second member reflective surface are located within the interior of said fluid conduit tube; and
ii) said optically clear portion is aligned between and collinear with said first member and said second member reflective surfaces.

8. The sensor device of claim 7, wherein said optically clear portion is positioned radially outward from the optical alignment of said first member and second member reflective surfaces, whereby the travel of electromagnetic radiation reflected off said first member reflective surface and to said second member reflective surface is fully within the molded fluid conduit tube.

9. The sensor device of claim 8, further comprising an opaque material between said first member reflective surface and said optically clear portion, said opaque material preventing the transmission of electromagnetic radiation therethrough.

10. The sensor device of claim 7, wherein the disposable cell includes an inlet and an outlet, the disposable cell being configured to accommodate flow of the fluid from the inlet, to the optical inset module and to the outlet.

11. The sensor device of claim 1, wherein the disposable cell is a container having first and second ends and an interior space for a fluid; and:
i) the reflective surfaces of the first and second members are at least partially located in the interior space of said container, and
ii) the third member has an optically clear window collinearly arranged with said first and second reflective surfaces.

12. A sensor device comprising a sensor module and a disposable optical inset module configured to dock with the sensor module,
said sensor module being reusable and having an energy source and a detector thereof; and
said disposable inset module includes:
(a) a cell comprising a conduit or container having an interior that contains a fluid when in use, a first member having a reflective surface and a second member having a reflective surface, said first and second member reflective surfaces being at least partially within the interior of the conduit or container and able to reflect energy emanating from the sensor module;
(b) said first member reflective surface and said second member reflective surface are in substantial alignment with each other, whereby energy originating from the sensor module, when having the disposable optical inset module docked therewith, is reflected off said first member reflective surface, travels to and then is reflected off one or more particulates of the fluid or travels to and then is reflected off said second member reflective surface; and
(c) a third member having a surface that permits transmission therethrough of energy reflected off one or more particulates of the fluid, said third member surface being disposed between said first member surface and said second member surface, said third member surface being substantially parallel to the travel of energy between the first member and second member surfaces.

13. The sensor device of claim 12, wherein the sensor device is selected from the group consisting of a turbidity sensor, a pH sensor, a particle size sensor, a protein concentration sensor, and combinations thereof.

14. The sensor device of claim 12, wherein said first member and second member have respective reflective surfaces having a mirrored coating.

15. The sensor device of claim 12, wherein said first member and said second member reflective surfaces are selected from the group consisting of gold, aluminum, silver, nickel, combinations thereof, alloys thereof and polymers containing same.

16. The sensor device of claim 12, wherein said third member surface is transparent to the energy emanating from the sensor module.

17. The sensor device of claim 12, wherein the first member and the second member extend beyond the third member and the energy reflects off objects between the first and second members.

18. The sensor device of claim 12, wherein the cell is a disposable flowcell comprising said inset module and:
a molded fluid conduit tube having first and second ends and an interior for passing a fluid therebetween, said tube having an energy transparent portion that extends less than the full circumference of the tube;
said first member reflective surface and said second member reflective surface are located at least partially within the interior of said fluid conduit tube; and
said energy transparent portion is aligned between and collinear with said first member and said second member reflective surfaces.

19. The sensor device of claim 18, wherein said energy transparent portion is positioned radially outward from the alignment of said first member and second member reflective surfaces, whereby the travel of energy reflected off said first member reflective surface and to said second member reflective surface is within the molded fluid conduit tube.

20. The sensor device of claim 19, further comprising an energy blocking material between said first member reflective surface and said energy transparent portion, said energy blocking material preventing the transmission of electromagnetic radiation therethrough.

21. The sensor device of claim 18, wherein the disposable cell includes an inlet and an outlet, the disposable cell being configured to accommodate flow of the fluid from the inlet, to the inset module and to the outlet.

22. The sensor device of claim 12, wherein the disposable cell is a container having first and second ends and an interior space for a fluid; and:
i) at least one of said reflective surfaces is located in the interior space of said container, and
ii) the third member has an energy transparent window is collinearly arranged with said one or more reflective surfaces.

* * * * *